(12) United States Patent
Kunz et al.

(10) Patent No.: US 6,429,022 B1
(45) Date of Patent: Aug. 6, 2002

(54) INTEGRATED-OPTICAL SENSOR AND METHOD FOR INTEGRATED-OPTICALLY SENSING A SUBSTANCE

(75) Inventors: Rino Kunz, Steinmaur; Max Wiki, Brugg; Philipp Zeller, Zollikerberg, all of (CH)

(73) Assignee: CSEM Centre Suisse d'electronique et de Microtechnique SA

( * ) Notice: Subject to any disclaimer, the term of this patent is extended or adjusted under 35 U.S.C. 154(b) by 0 days.

(21) Appl. No.: 09/510,609

(22) Filed: Feb. 22, 2000

(30) Foreign Application Priority Data

Feb. 25, 1999 (EP) .............................. 99103730

(51) Int. Cl.$^7$ .............................................. G01N 21/01
(52) U.S. Cl. ..................................... 436/164; 422/82.11
(58) Field of Search .................... 422/82.11, 82.09; 436/172, 164; 385/12, 37; 356/328

(56) References Cited

U.S. PATENT DOCUMENTS

| | | | |
|---|---|---|---|
| 5,071,248 A | * 12/1991 | Tiefenthaler et al. |
| 5,082,629 A | * 1/1992 | Burgess, Jr. et al. |
| 5,313,264 A | * 5/1994 | Ivarsson et al. |
| 5,442,169 A | 8/1995 | Kunz |
| 5,455,178 A | * 10/1995 | Fattinger |
| 5,577,137 A | 11/1996 | Groger et al. |
| 5,623,561 A | 4/1997 | Hartman |
| 5,738,825 A | 4/1998 | Rudigier et al. |
| 5,822,472 A | * 10/1998 | Danielzik et al. |

FOREIGN PATENT DOCUMENTS

| | | | |
|---|---|---|---|
| WO | WO 92/19976 | 11/1992 |
| WO | WO96/35940 | 11/1996 |
| WO | WO 97/06422 | 2/1997 |
| WO | WO 97/29362 | 8/1997 |
| WO | WO 9809156 | * 3/1998 |

OTHER PUBLICATIONS

R. E. Kunz and J. Dubendorfer, Miniature integrated–optical wavelength analyzer chip; 1995 Optical Society of America; Paul Scherrer Institute, Badenerstrasse569.CNH–8048 Zurich, Switzerland.

Dongho Shin, Sorin Tibuleac, Theresa A. Maldonado, Robert Magnusson, Thin–film optical filters with diffractive elements and waveguides; 1998 Society of Photo–Optical Instrumentation Engineers; Sep. 1998.

M. Wiki, J. Dubendorfer, R. E. Kunz, Spectral beam sampling and control by a planar optical transducer, International Journal Devoted to Research and Development of Physical and Chemical Transducers, vol. A67 (1998).

R. E. Kunz, Totally Integrated Optical Measuring Sensors, Chemical, Biochemical, and Environmental Fiber Sensors III, The International Society for Optical Engineering, vol. 1587, Sep. 1991.

R. E. Kunz, Miniature integrated optical modules for chemical and biochemical sensing, Sensors and Actuators, B, Chemical. (1997) 13–28.

* cited by examiner

Primary Examiner—Jeffrey Snay
(74) Attorney, Agent, or Firm—Oppedahl & Larson LLP

(57) ABSTRACT

The integrated-optical chemical and/or biochemical sensor comprises a resonant waveguide grating structure (1.1, 1.2, . . . ), e.g., a chirped grating. By illumination with incident light (21), a resonant electromagnetic field is excited in the grating structure (1.1, 1.2, . . . ). At least one parameter of the incident light, e.g., the angle of incidence ($\theta_1$) or the wavelength ($\lambda_{-1}$), is varied. Light (23) excident from the grating structure (1.1, 1.2, . . . ) is detected by detectors (4.1, 4.2, . . . ). Optionally, means for providing a feedback from the detectors (4.1, 4.2, . . . ) to the light sources may be provided, thus establishing a controlled closed-loop system. Hence independent simultaneous measurements in a multiple arrangement of such sensors (S1, S2, . . . ) is made possible. Moreover, a much higher density of sensors (S1, S2, . . . ) results.

23 Claims, 10 Drawing Sheets

INTEGRATED-OPTICAL SENSOR AND METHOD FOR INTEGRATED-OPTICALLY SENSING A SUBSTANCE

The invention relates to a chemical and/or biochemical integrated-optical sensor, a multiple arrangement of a plurality of such sensors and a method for integrated-optically sensing a substance, according to the preambles of the independent claims.

Many present and upcoming applications of chemical and/or biochemical microsystems, especially for application areas such as medical, food and environmental, require the detection of several analytes being simultaneously present in a liquid. One well-known and advantageous type of detection is optical. An important class of such optical sensors are integrated optical (IO) sensors comprising a chip with a waveguide and sensing biolayers. An example for this type of device is disclosed in WO 92/19976. Other patents have also been applied for in recent years and work has been published by various groups worldwide.

Different sensing principles are being used in IO chemical and/or biochemical sensors. These principles and arrangements allow one to integrate many sensing pads or sensors on one single chip for realizing on-chip referencing and complex analyte sensing.

In this document, the term "sensor" stands for "sensing" elements used for chemical and/or biochemical measurements as well as for "referencing" elements used for reference measurements. This is to avoid ambiguities, since there are many aspects which apply to both, sensing and referencing sensors, and referencing sensors can be considered to just represent a special type of measuring sensors, used to perform on-chip referencing.

It is known from the state of the art to arrange IO sensors in an array pattern. However, only one-dimensional IO sensor arrays permit independent simultaneous ("parallel") measurements. More complex, e.g., two-dimensional, sensor arrays seriously suffer from crosstalk between the various IO channels, i.e., the optical signals cannot be separated in an acceptable way.

A further disadvantage of known multiple IO sensor arrangements is that the sensors require too much of chip area, leading to very big chips and also to a small ratio between active and passive area. (In this document, the term "active area" denotes the area of the IO sensor in which an interaction of the measurand with the light takes place.) They also need too much of (bio-)chemical area, since this is not efficiently used. Another problem with presently known array detection schemes is that the efficiency of on-chip referencing is limited by the large distance between sensing and referencing sensors due to their large size.

It is an object of the invention to provide a multiple arrangement of IO sensors which makes possible independent simultaneous ("parallel") measurements with the sensors. It is a further object to provide an IO sensor for use in such a multiple arrangement. It is still a further object to indicate a method for integrated-optically sensing a chemical and/or biochemical substance using such a sensor.

The invention also aims at removing other drawbacks of the state-of-the art solutions for achieving high-density array IO sensors. In particular, it is another object of the invention to provide a multiple arrangement of IO sensors with:

more efficient on-chip referencing,
chip and system miniaturization, i.e., more sensors per chip area (in the case of a two-dimensional sensor) or per volume (in the case of a three-dimensional sensor),
less chemicals needed for chip biocoating, and
less analyte volume needed due to reduced chip area for performing same task.

To take full advantage for practical applications, the following constraints shall be taken into account:

the sensitivity is maintained or increased with respect to the conventional solutions, and
the dynamic range is maintained or increased with respect to the conventional solutions.

The objects are resolved by the IO sensor, the multiple arrangement of IO sensors and the method as defined in the independent claims.

The integrated-optical chemical and/or biochemical sensor according to the invention comprises a resonant waveguide grating structure defining a surface plane; means for emitting electromagnetic radiation towards the resonant waveguide grating structure, the means for emitting electromagnetic radiation comprising means for varying at least one parameter of the emitted electromagnetic radiation, the mutual arrangement of the resonant waveguide grating structure and the means for emitting electromagnetic radiation being such that the angles of incidence with respect to a normal line on said surface plane are greater than −90° and smaller than +90°; and detector means for detecting electromagnetic radiation excident from the resonant waveguide grating structure under angles of excidence with respect to a normal line on said surface plane greater than −90° and smaller than +90°.

The multiple one-, two- or three-dimensional arrangement according to the invention comprises a plurality of sensors as defined above.

The method for integrated-optically sensing a chemical and/or biochemical substance according to the invention comprises the steps of emitting electromagnetic radiation towards the resonant waveguide grating structure, the angles of incidence with respect to a normal line on said surface plane being greater than −90° and smaller than +90°; exciting a resonant electromagnetic field in the resonant waveguide grating structure by means of the emitted electromagnetic radiation; causing an interaction of the substance with the resonant electromagnetic field; varying at least one parameter of the emitted electromagnetic radiation; and detecting electromagnetic radiation excident from the resonant waveguide grating structure under angles of excidence with respect to a normal line on said surface plane greater than −90° and smaller than +90°.

According to the invention, the functionality of the measuring pads is increased. The measuring pad geometry is adapted to the sensing principle, to the overall chip geometry, and to the particular application. The efficiency of light collection (in general: "optical transfer processes") is enhanced. Use is made of additional on-chip and/or off-chip and/or general degrees of freedom. The area required for performing the sensing task is reduced, especially by reducing the area required by a single measuring pad in an array, and by increasing the ratio between active and passive chip area.

Hence, a much higher density of sensors results for single-chip IO sensor arrangements, leading to several advantages as is described below. As an example, we will consider advantages for on-chip referencing, which is eased due to the smaller distance, and because multiple referencing sensors can be used per sensing pad, e.g. one on top and one below or left and right or distributed around etc. This is especially important for sensors with very high sensitivities, since they are more affected by unspecific effects such as temperature and signal drift due to chemical and physical fluctuations and chip deformation.

The invention is described in greater detail hereinafter, compared with the prior art, relative to the attached schematic drawings.

Figure 1:
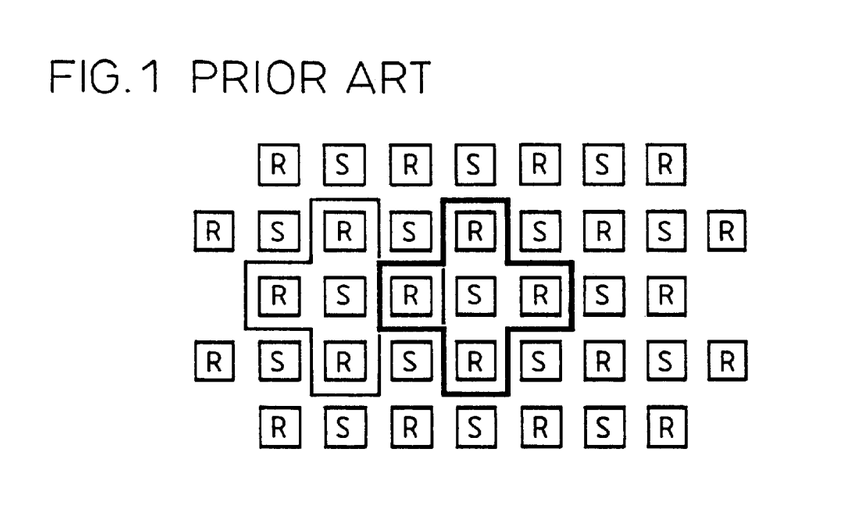
FIG. 1 shows an IO sensor with a two-dimensional array of measuring pads.
Figure 2:
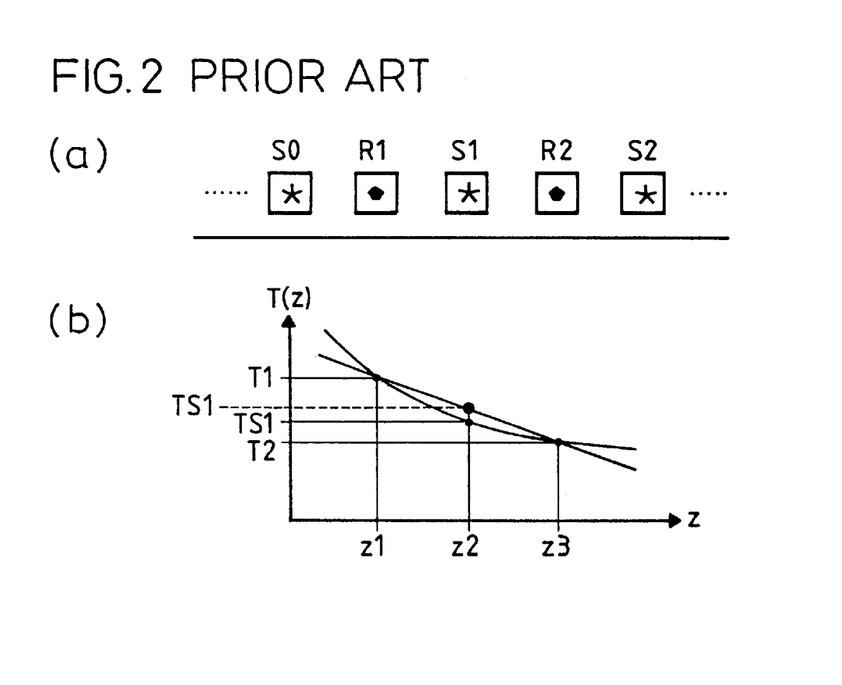
FIG. 2 shows the influence of disturbances and its dependence on the distance and/or size of the sensing pads.
Figure 3:
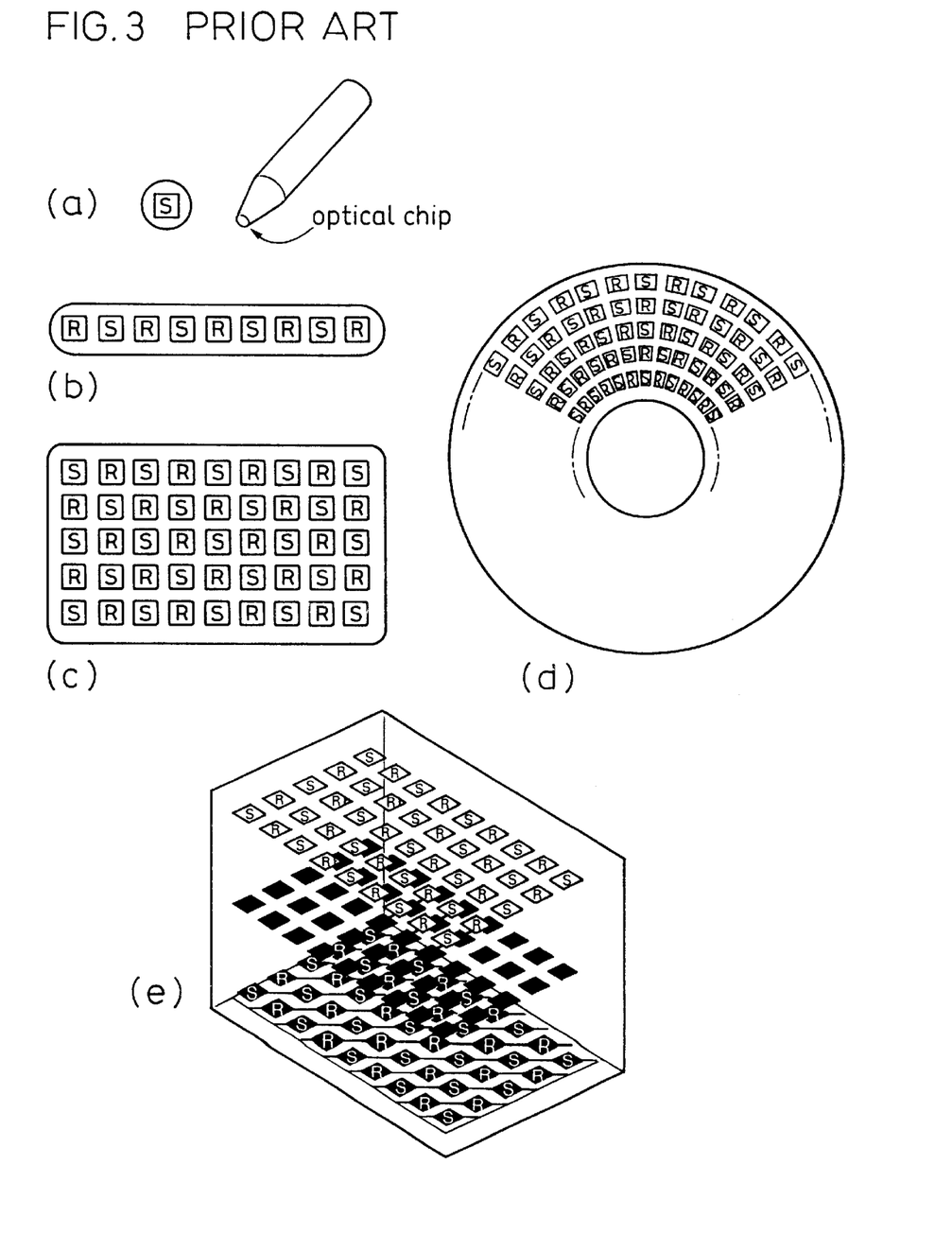
FIG. 3 shows applications of IO sensors for high-density zero-, one-, two- and three-dimensional sensing.

The FIGS. 1–3 serve to illustrate the motivation for the invention. FIG. 1 shows an example of a two-dimensional sensor array featuring sensing pads S and referencing pads R. These are distributed in a manner to have the most sensitive sensing pads S surrounded by referencing pads R on all sides. This ensures that on-chip referencing is also effective to eliminate gradients of disturbances. The measuring pads S, R are drawn as rectangles; however, they may have any other geometric form such as circles, triangles etc.

The influence of disturbances, e.g., temperature gradients, and its dependence on the distance and/or size of the sensing pads is illustrated in FIGS. 2(a) and (b). FIG. 2(a) shows a linear (i.e., one-dimensional) array of measuring pads S0, R1, S1, R2, S2, ..., where a sensing pad S1 is surrounded by two referencing pads R1, R2. FIG. 2(b) shows two different temperature distributions T(z) versus a position z. The positions of the pads R1, S1, R2, in FIG. 2(a) are z1, z2 and z3, respectively. For compensation of an undesirable temperature effect, the reference signals of the pads R1 and R2 are linearly interpolated. In case of a linear gradient, the compensation is perfect; in case of a nonlinear gradient, the quality of compensation depends on the degree of nonlinearity and on the distance of the pads. While there is only minor influence on the global nonlinearity of the disturbance, the present invention achieves a marked improvement by reducing the pad size, which reduces the degree of the nonlinearity on a local scale, i.e., in the region between the referencing pads.

A size reduction of the measuring pads is also important for applications such as the tip sensor shown in FIG. 3(a). Such a tip sensor with, e.g., one sensing S pad on a pen tip, is in fact a zero-dimensional IO sensor. It is important to reduce the tip size in order to get a high spatial resolution and/or to be able to use the sensor in locations where there is not much space, e.g., in the body of human beings or animals. If a high degree of size reduction is achieved, small arrays of one-dimensional or two-dimensional arrangements can also be used on such tip-sensors (e.g., one sensing pad surrounded by four referencing pads).

Very important applications are high-density one-dimensional and two-dimensional sensing, as is shown in FIGS. 3(b) and 3(c), (d), respectively. The advantages of increasing the pad density per unit of length (FIG. 3(b)) and per unit of area (FIGS. 3(c) and (d)) have already been stated above.

Making further use of measuring pad size reduction, one can further increase the pad density also per volume in three-dimensional arrangements, an example of which is given in FIG. 3(e). This is especially interesting for gas sensing.

Figure 4:
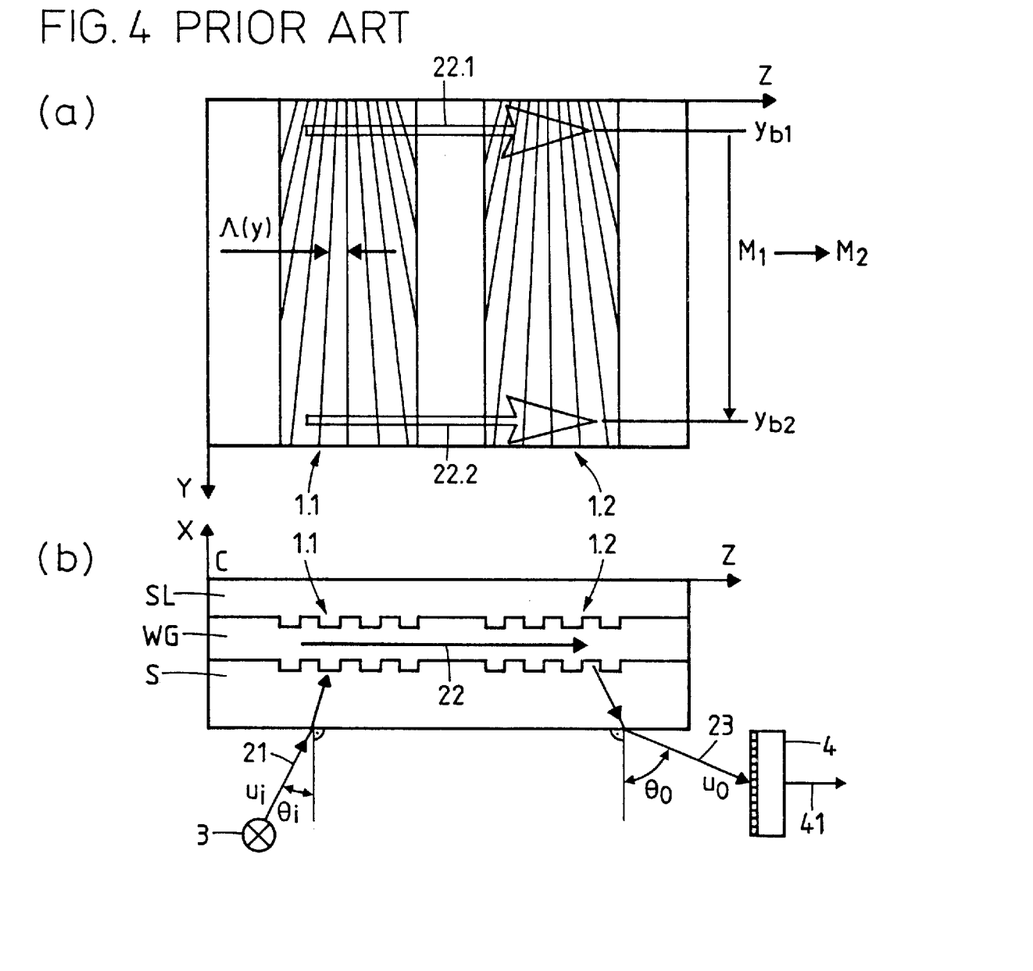
FIG. 4 shows an IO sensor according to the state of the art with a pair of chirped gratings.

FIG. 4 shows a sensor known from the state of the art which has been used in recent years for performing chemical and biochemical measurements and is disclosed in the following publications:

WO 92/19976;

R. E. Kunz, "Totally Integrated Optical Measuring Sensors," Proc. SPIE, Vol. 1587, 98–113 (1992);

R. E. Kunz, "Miniature Integrated Optical Modules for Chemical and Biochemical Sensing", Sensors and Actuators B, Vol. 38–39, 13–28 (1997).

FIG. 4(a) is a top view, and FIG. 4(b) is a side view of the sensor.

The sensor of FIG. 4 comprises a planar optical waveguide WG sandwiched between a substrate S and a sensing layer SL, with a cover medium C. For reasons of simplicity, only one waveguide layer and only one sensing layer is shown; however, the waveguide and/or the sensing layer could be built up of a plurality of layers. The sensor makes use of a pair of chirped grating couplers 1.1, 1.2, an input grating coupler 1.1 and an output grating coupler 1.2. In the side view of FIG. 4(b), gratings are shown on both surfaces of the waveguide WG; it is, however, clear to a person skilled in the art that a resonant waveguide grating structure can be realized in other ways, e.g., by a grating on only one surface of the waveguide WG. The well-known input coupler resonance condition for achieving maximum coupling efficiency is given by $$N = n_a \sin \theta_i + m_g \lambda / \Lambda, \quad (1)$$

where N is the effective index, $\theta_i$ is the angle of incidence of an input beam measured in an ambient medium with a refractive index $n_a$, and $m_g$ is the grating diffraction order. A resonance condition analogous to Eq. (1) also holds for the output coupler. Light is typically emitted from a light source 3, incoupled in the form of an incident plane wave $u_i$, 21, guided as a mode 22 in the waveguide WG and is outcoupled in the form of an excident plane wave $u_o$, 23, under an angle $\theta_o$. In the sensor of FIG. 4, all waveguide parameters such as the waveguide thickness or the refractive indices are spatially uniform, whereas the grating periods $\Lambda(y)$ linearly depend on the lateral coordinate y; in other embodiments, the waveguide thickness and/or the refractive indices could depend on y. The effective index N depends, among other parameters, also on the refractive index of the material SL on the waveguide surface and consequently on a measurand M on the waveguide surface. From the resonance condition Eq. (1) it follows that a mode position $Y_{b1}$ changes to a position $Y_{b2}$ upon a change of the measurand's value from $M_1$ to $M_2$. The guided mode 22 in the sensor of FIG. 4 is thus called an IO light pointer (IOLP). The mode position $Y_{b1}$ is detected by a detector 4 arranged to detect the outcoupled light 23, yielding an output signal 41. The detector can be realized as, e.g., a charge-coupled device (CCD) array.

The sensor of FIG. 4 has several disadvantages. Apparently, its dynamic range is proportional to its width (in y direction). Therefore, in order to obtain a high dynamic range, the sensor width and sensor area have to be very large, which is undesirable for the reasons discussed above. As a second disadvantage, the quality of the sensor signal 41 is reduced by imperfections in the waveguide WG, the sensing layer SL, the substrate S etc., e.g., by light scattering. Moreover, the chirp of the grating 1 and the waveguide parameters cannot be made perfectly homogeneous over the entire width of the sensor, which reduces the sensor sensitivity.

Figure 5:
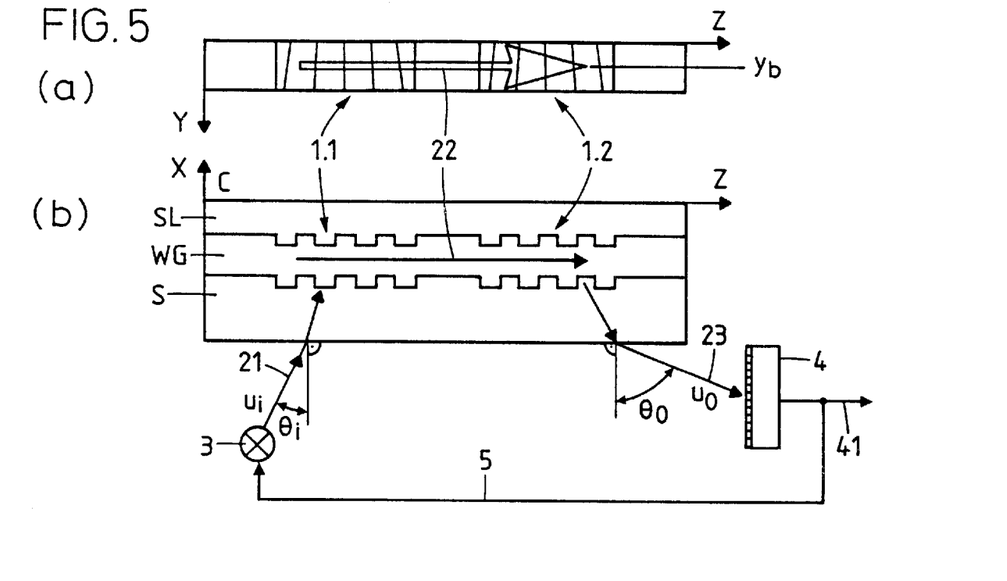
FIGS. 5 and 6 show a first and a second embodiment, respectively, of an IO sensor according to the invention.

FIG. 5 shows a first embodiment of an IO sensor according to the invention in a top view (FIG. 5(a)) and a side view (FIG. 5(b)). The sensor is provided with two chirped gratings 1.1, 1.2 as in the arrangement of FIG. 4. However, the width (in y direction) of the sensor is strongly reduced compared with that of FIG. 4. The size of the entire sensing unit (i.e., the pair of grating pads 1.1, 1.2) in the y-direction is preferably smaller than 5 times the width of the guided mode 22 or smaller than 1 mm. With such a small lateral dimension, the dynamic range of a conventional sensor according to FIG. 4 would be unacceptably low. In order to overcome this impediment, the sensor according to the invention actively clamps or stabilizes the lateral position $Y_b$ of the guided mode 22 to be constant by means of an additional degree of freedom. The additional degree of freedom may be, e.g., the wavelength of light $\lambda$; other possible degrees of freedom are the angle of incidence $\theta_i$ or the spectral light distribution. The effect of changing the wavelength on the IOLP position $y_b$ has been investigated and demonstrated in the following publications:

R. E. Kunz and J. Dübendorfer, "Miniature Integrated Optical Wavelength Analyzer Chip," Optics Letters, Vol. 20, 2300–2303 (1995);

M. Wiki, J. Dübendorfer and R. E. Kunz, "Spectral Beam Sampling and Control by a Planar Optical Transducer," Sensors and Actuators A, Vol. 67/1–3, 120–124 (May 15, 1998).

A feedback is provided from the detector 4 to the light source 3, thus establishing a controlled closed-loop system. Hence, the drawbacks discussed with reference to FIG. 4 are eliminated by changing the wavelength $\lambda$ of the light source 3 in order to keep the IOLP position $y_b$ fixed at all times. A substantial reduction in sensor size is achieved by compensating the effect of the measurand M. The dynamic range of this sensor is no longer determined by the physical size of the sensing unit, but by the range $\Delta\lambda$ in which the wavelength $\lambda$ can be varied, and of the chirp of the grating coupler 1.1. Inhomogeneities of the sensor are of minor importance because the sensor width and area are extremely small. Other components of the sensor are described in detail with reference to FIG. 4 and need no further explanation. Typical materials and parameters of the sensor are the following. The substrate S is made of, e.g., polycarbonate ($n_S$=1.57), glass, e.g., AF45 ($n_S$=1.52) or quartz ($n_S$=1.45), or silicon. It also may consist of several materials, e.g., of an $SiO_2$ layer on silicon. The waveguiding film WG is made of, e.g., $TiO_2$ ($n_{WG}$=2.35), $Si_3N_4$ ($n_{WG}$=1.8–2.1) or $Ta_2O_5$ ($n_{WG}$=2.20); a combination of several layers is also possible. Typical thicknesses of waveguiding films WG are in the range between 100 nm and 300 nm, e.g., 150 nm. The sensing layer SL consists of one or several substances to be sensed. Optionally, it may include one or several layers of proteins ($n_{SL}$=1.35–1.55) which are capable of binding (bio-)chemical substances to be sensed. Such substances are typically transported to the sensor in an aqueous solution ($n_C$=1.33). The light source 3 is typically narrow-band light source such as a laser emitting a wavelength of, e.g., 632.8 nm, 650 nm, 785.1 nm or 980 nm. Typical grating periods $\Lambda$ are in the range between 250 nm and 500 nm. Singly periodic, multiply periodic and/or superposed gratings 1.1, 1.2 may be used. According to the invention, a plurality of wavelengths, incoupling angles and/or polarizations may be present at the same time. The wavelengths, incoupling angles and/or polarizations may be discrete or exhibit a broad-band distribution.

Figure 6:
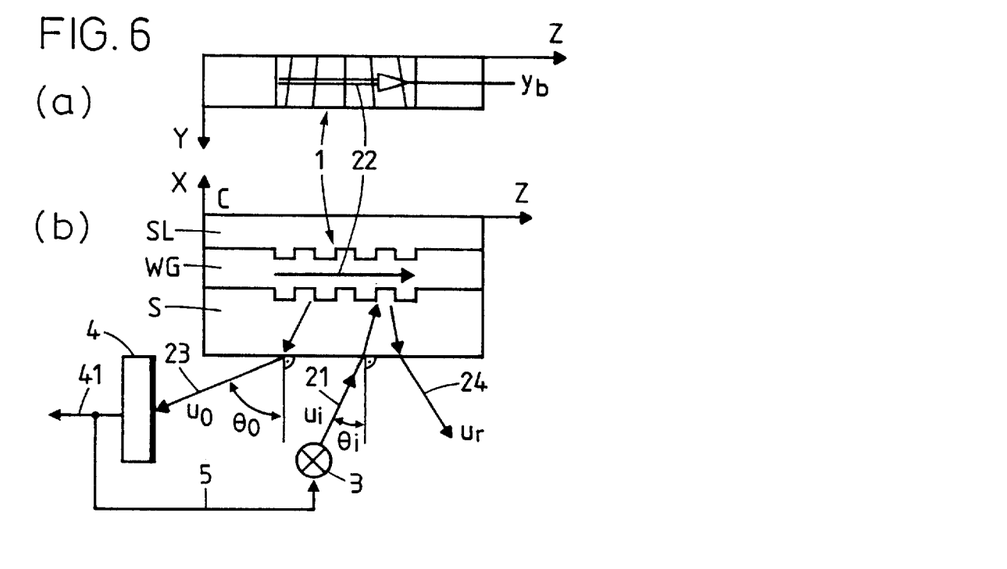

A further reduction of the sensor dimensions can be achieved with the sensor according to the invention shown in FIG. 6 (top view, FIG. 6(a), side view, FIG. 6(b)), which is a further development of the embodiment of FIG. 5. In this embodiment, the sensor dimensions are reduced also in the z direction by means of introducing yet another degree of freedom, for example by using a single grating coupler 1 working at two (or more) different diffraction orders. Yet another degree of freedom could by introduced by observing scattered light emitted from the grating structure (cf. FIG. 7). In the example of FIG. 6, the diffraction order $m_g$=1 is used for incoupling and the diffraction order $m_g$=−2 is used for outcoupling. Hence the diffraction orders $m_g$=0 (reflected) and $m_g$=1, forming the wave $u_r$, 24, do not disturb the sensor signal by lessening the signal-to-noise ratio. Of course, higher diffraction orders $|m_g|$>2 can also be used for in- or outcoupling.

Figure 7:
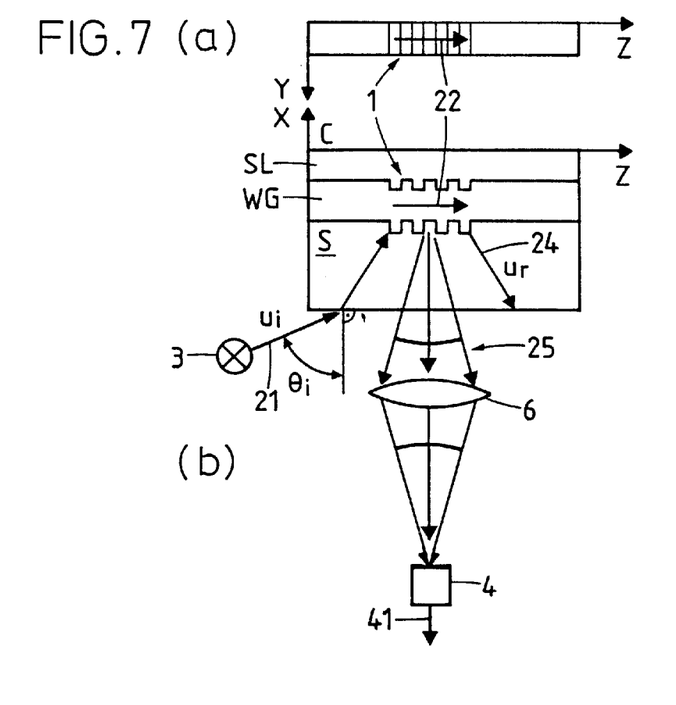
FIG. 7 shows a further embodiment of an IO sensor according to the invention.

FIG. 7 shows a further embodiment of an IO sensor according to the invention. Instead of measuring and controlling the y position of the resonantly outcoupled light, the intensity distribution of light 25 scattered in the region of the resonant waveguide grating structure 1 is measured Such measurement can be formed by imaging at least a part of the resonant waveguide grating structure 1 onto a light intensity detector 4, e.g., a photodiode, by means of an imaging system 6. The sensor could alternatively dispense with the imaging system 6 if the light detector 4 was placed near the resonant waveguide grating structure 1 (cf. FIG. 11(a)). In another embodiment (not shown), the scattered light 25 could also be guided to a detector by an optical fiber. Light scattering may have "natural" causes such as imperfections in the resonant waveguide grating structure 1, or "artificial" causes such as roughening of the waveguide surface or implanted imperfections in the waveguide WG.

The intensity of the scattered light 25 is a measure for the photon density in the region of the resonant waveguide grating structure 1, which is high if a resonant electromagnetic field 22 is excited by the incident light 21 and low otherwise. By measuring the intensity of the scattered light 25, undesirable contributions of the diffraction orders $m_g$=0 (reflected) and $m_g$=1, 24, to the measured signal 41 are avoided, thus yielding a better signal-to noise ratio. The embodiment of FIG. 7 is an example of resonant incoupling and non-resonant outcoupling. A feedback loop (here not shown) for controlling a parameter of the incident light, e.g., its wavelength, could be provided as in FIGS. 5 and 6.

Figure 8:
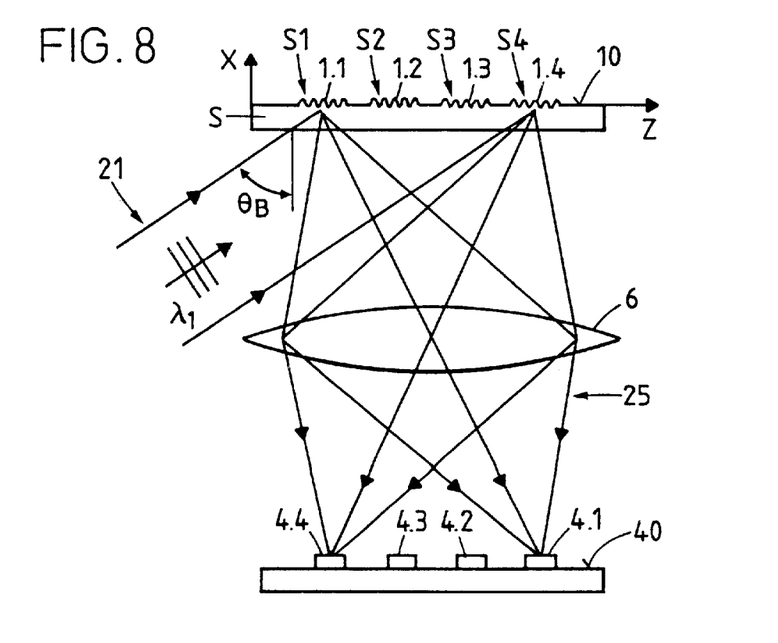
FIGS. 8 and 9 show two embodiments of a multiple arrangement of IO sensors according to the invention.

FIG. 8 shows a side view of an embodiment of a multiple arrangement of IO sensors according to the invention. A plurality of IO sensors S1–S4 are arranged in, e.g., an array in a surface plane 10 on a transparent substrate S. The details of the resonant waveguide grating structures 1.1–1.4 can be similar as those in FIGS. 5–7 and are not shown in FIG. 8. Alternatively, filter structures as described in D. Shin, S. Tibuleac, Th. A Maldonado and R. Magnusson, "Thin-film optical filters with diffractive elements and waveguides", Opt, Eng. 37(9), 2634–2646 (September 1998) can be used. The IO sensors S1–S4 of this multiple arrangement are operated by resonant incoupling and non-resonant outcoupling, as the sensor shown in FIG. 7. Preferably one single light beam 21 illuminates all the sensors S1–S4; alternatively, a plurality of light beams can be used. The angle of incidence is preferably chosen to be the Brewster angle $\theta_B$; then, if the incoming light is p polarized, undesirable reflected light is reduced almost to zero. For a typical sensor with a substrate S made of polycarbonate ($n_S$=1.571), a $TiO_2$ waveguiding film WG ($n_{WG}$=2.350) having a thickness of 150 nm, a protein layer ($n_{SL}$=1.45) as a sensing layer SL and a cover C of water ($n_C$=1.328), and the wavelength of the incident light being $\lambda$=785 nm, the Brewster angle is $\theta_B$=57.5°. For a resonant incoupling in the diffraction order $m_g$=1, a grating period of $\Lambda$=306 nm must be provided, according to Eq. (1).

The surface plane 10 containing the resonant waveguide grating structures 1.1–1.4 is imaged onto a surface plane 40 containing a plurality of light intensity detectors 4.1–4.4 by an imaging system 6. In analogy to FIG. 7, the intensity of light 25 scattered in the region of the resonant waveguide grating structures 1.1–1.4 is measured by the light detectors 4.1–4.4. Preferably each detector 4.1–4.4 is biuniquely assigned to a certain resonant waveguide grating structure 1.1–1.4. In a measurement, a parameter of the incident light 21, preferably the wavelength $\lambda_1$, is varied with time in order to excite resonant electromagnetic fields in the resonant waveguide grating structures 1.1–1.4.

Analogously, the arrangement of FIG. 8 can also be operated by imaging resonantly outcoupled light in a chosen diffraction order onto the detector.

Figure 9:
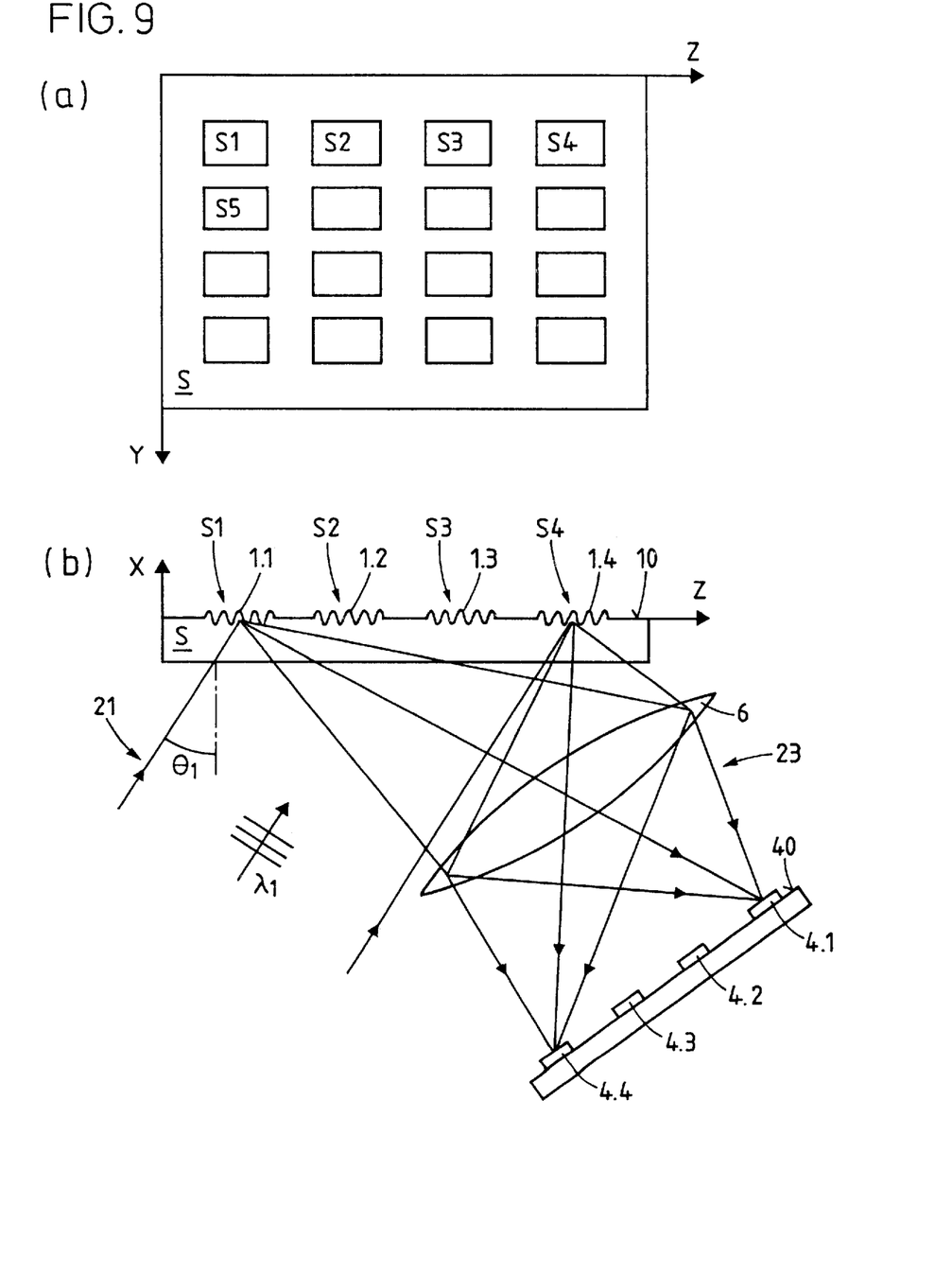

FIG. 9 shows a preferred embodiment of a multiple arrangement of IO sensors S1, S2, . . . according to the invention in a top view (FIG. 9(a)) and a side view (FIG. 9(b)). The sensors S1, S2, . . . are arranged in a two-dimensional array on a substrate S, e.g., in equally spaced rows and columns. The sensors S1, S2, . . . can be used for obtaining a measuring signal or a referencing signal (cf. FIG. 1), i.e., some of them could also be referenced as R. They are illuminated preferably by a single incident light beam 21 with a defined wavelength $\lambda_1$ under a defined angle of incidence $\theta_1$. Alternatively, the incident light 21 could provide a wide range of wavelengths, different polarizations and/or a wide range of angles of incidence, or could contain a plurality of discrete wavelengths and/or of discrete angles of incidence.

A parameter or several parameters of the incident light 21 such as the wavelength $\lambda_1$, the angle of incidence $\theta_1$, the polarization and/or the wavefront is varied during the measurement. If the resonance conditions are fulfilled, the incident light 21 excites a resonant electromagnetic field in at least one resonant waveguide grating structure 1.1, 1.2, . . . As a measure for resonance, e.g., the light distribution of resonantly outcoupled light 23 is detected for each resonant waveguide grating structure 1.1, 1.2, . . . by light position detectors 4.1, 4.2, . . . , e.g., CCD arrays. For this purpose, an imaging system 6 can be arranged between the resonant waveguide grating structures 1.1, 1.2, . . . and the position detectors 4.1, 4.2, . . . Preferably each position detector 4.1, 4.2, . . . is biuniquely assigned to a certain resonant waveguide grating structure 1.1, 1.2, . . .

Instead of the imaging system 6, a cylindrical focusing optical system (not shown) can be used, the position detectors 4.1, 4.2, . . . lying in the focal plane 40 of the cylindrical optical system. The cylindrical optical system acts as means for the variation of the angle of excidence into a variation of light position on the detectors 4.1, 4.2, . . . ; in other words, it performs an optical Fourier transform of the outcoupled light 23.

Figure 10:
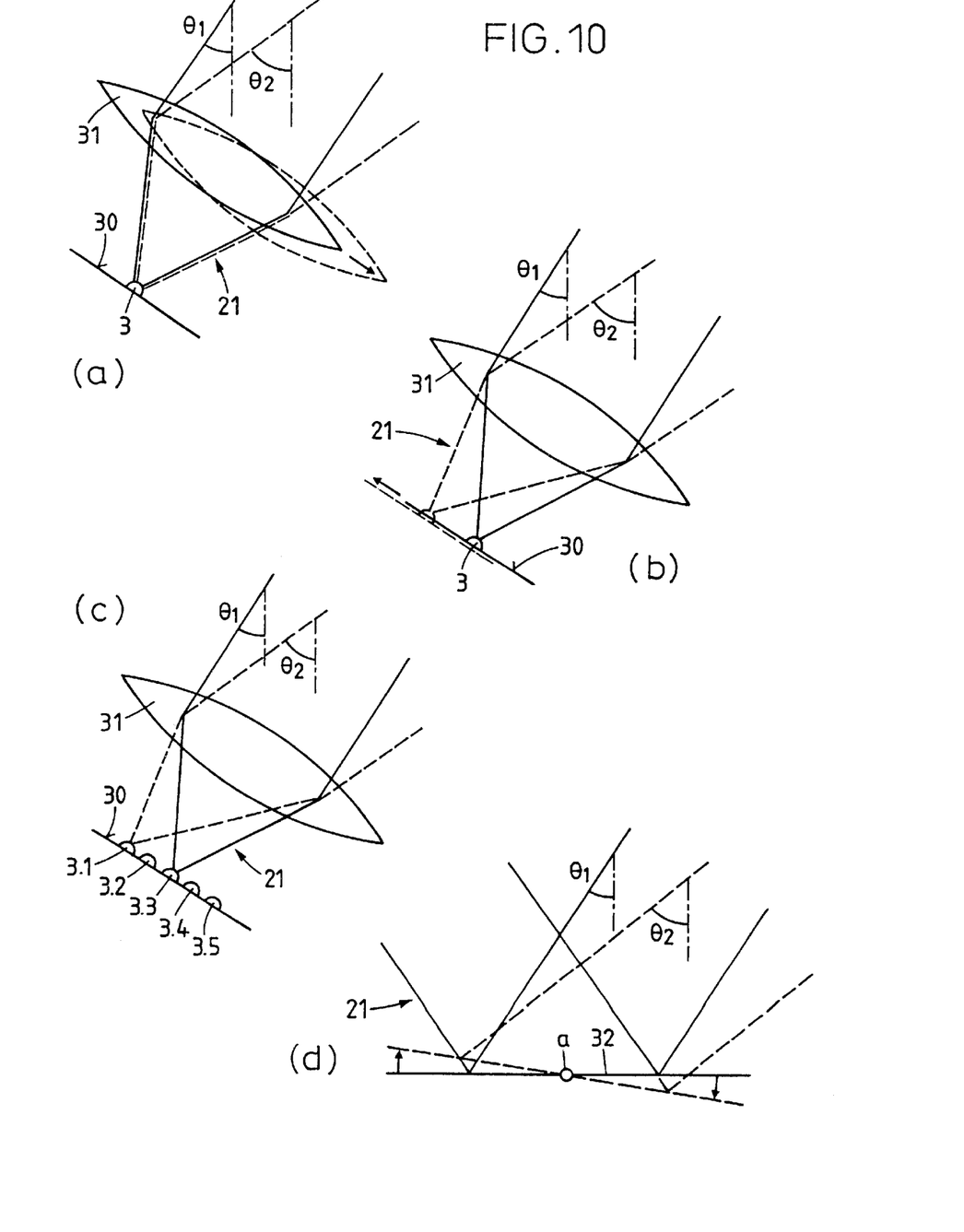
FIG. 10 shows means for varying the angle of incidence.

In FIG. 10, various means for varying the angle of incidence $\theta_1$ are shown. Light 21 is emitted by a point light source 3, e.g., a vertical cavity surface emitting laser (VCSEL), a distributed feedback (DFB) laser or a distributed Bragg reflector (DBR) laser, which lies in a focal plane 30 of a collimating optical system 31. In the embodiment of FIG. 10(a), the position of the optical system 31 is varied from a first position (full lines) to a second position (dashed lines), thus varying the angle of incidence from $\theta_1$ to $\theta_2$. In the embodiment of FIG. 10(b), the position of the point light source 3 is varied. The embodiment of FIG. 10(c) does not require any moving parts. Instead, a plurality of point light sources 3.1–3.5 arranged in the focal plane 30 of a collimating optical system 31 is provided. The angle of incidence $\theta_1$ is discretely varied by switching on different light sources 3.1–3.5. A further possibility for variation is the use of a mirror 32 rotatable around a rotation axis a as shown in FIG. 10(d). The variation of the angle of incidence can be used for exciting a resonant electromagnetic field in a resonant waveguide grating structure, but also in order to compensate for chip tolerances and/or to achieve a wider dynamic range.

A further embodiment of a multiple arrangement of IO sensors S1, S2, . . . according to the invention is shown in FIG. 11(a) in a side view. The resonant waveguide grating structures 1.1, 1.2, . . . can, e.g., be arranged in a two-dimensional array on a first substrate S as in FIG. 9. Various resonant waveguide grating structures 1.1, 1.2, . . . as discussed with reference to the previous figures can be used. In this embodiment, the angles of incidence are chosen to be near zero, i.e., $\theta_i$=0; this simplifies the illumination/readout configuration. Other angles of incidence as shown in the previous figures, e.g., the Brewster angle (cf. FIG. 8), are also possible. A typical waveguide has a substrate S made of polycarbonate ($n_S$=1.571), a $TiO_2$ waveguiding film WG ($n_{WG}$=2.350) having a thickness of 150 nm, a protein layer ($n_{SL}$=1.45) as a sensing layer SL and a cover C of water ($n_C$=1.328), and the wavelength of the incident light is 785 nm. From Eq. (1), it follows that a grating period of $\Lambda$=455 nm has to be provided for normal incidence ($\theta_i$=0).

In the embodiment of FIG. 11(a), an array of light intensity detectors 4.1, 4.2, . . . , e.g., a photodiode array, on a second substrate D is positioned close to the resonant waveguide grating structures 1.1, 1.2, . . . The light detectors 4.1, 4.2, . . . measure, e.g., the intensity of transmitted light (not shown) for the corresponding resonant waveguide grating structures 1.1, 1.2, . . . In comparison with FIGS. 7, 8 and 9, the embodiment of FIG. 11(a) presents the following differences: the transmitted light is measured instead of reflected light, and it is detected directly without an imaging system. The gap 8 between the first substrate S and the second substrate D can be used as a channel for an analyte, the flow of which is symbolized by arrows 81.1, 81.2.

The resonant electromagnetic fields in the resonant waveguide grating structures are excited by varying a parameter of the incident light, e.g., its wavelength $\lambda$. FIG. 11(b) shows a periodic variation of the wavelength $\lambda$, and FIG. 11(c) shows possible corresponding sensor output signals $s_1$, $s_2$, . . . versus time t. Minimums or dips 91.1, 91.2, . . . of the output signals $S_1$, $S_2$, , . . . are periodically detected at different times, i.e., at different wavelengths, if the sensors S1, S2, . . . and/or their environments are not exactly identical. Upon a change of the environments, e.g., when an analyte passes the sensors S1, S2, . . . , the positions of the dips 91.1, 91.2, . . . change, which is symbolized by arrows 92.2, . . . From such position changes 92.2, . . . of the dips 91.1, 91.2, . . . , information about the composition and/or the amount of the analyte is obtained. It may be useful to have a reference signal $S_1$, the dips 91.1 of which normally do not change their positions.

Figure 11:
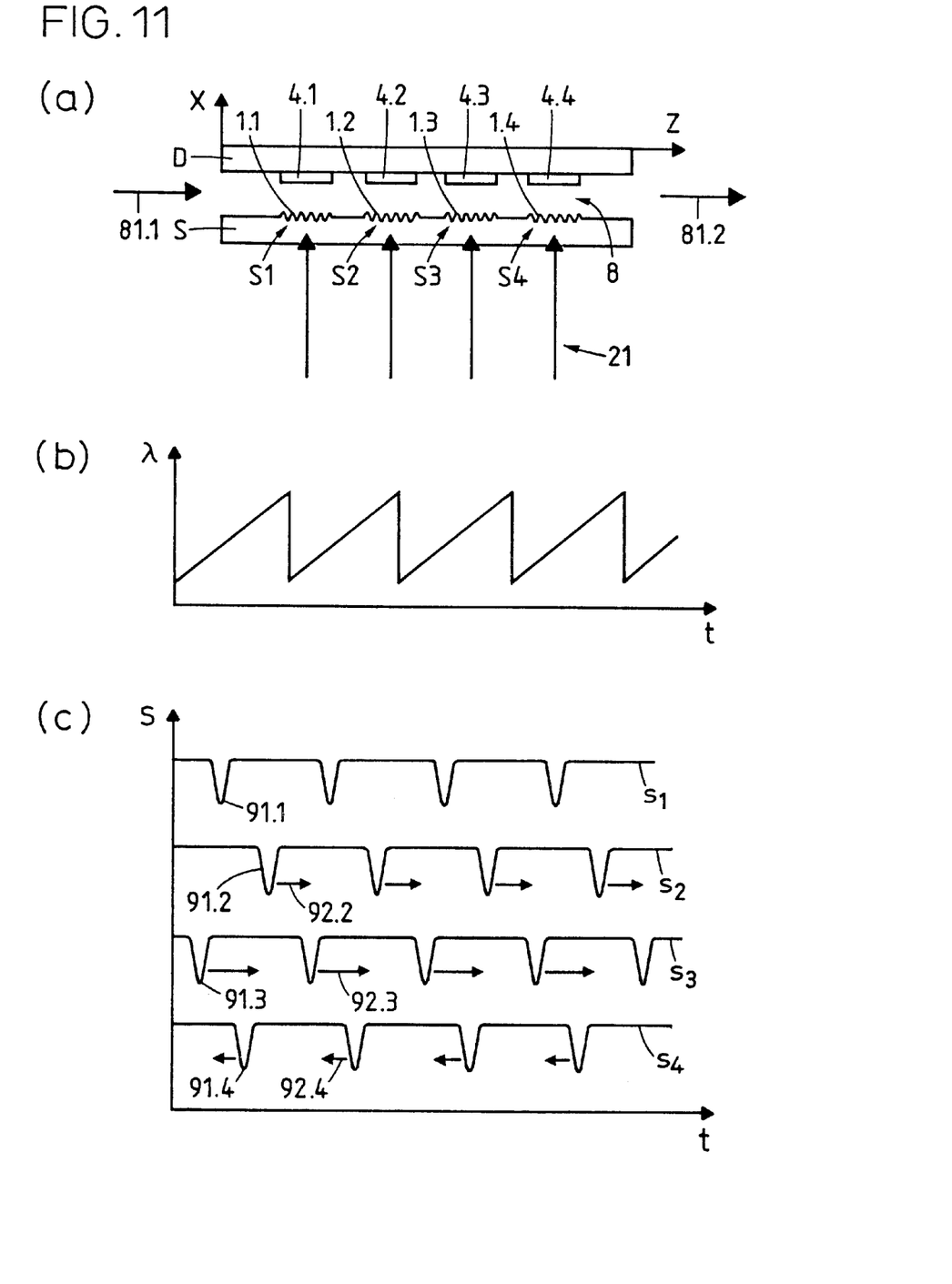
FIG. 11 shows a further embodiment of a multiple arrangement of IO sensors according to the invention, and the variation in time of the input wavelength and the output signals.

This arrangement is particularly fitted for measuring changes in refractive index absorption or scattering properties, or any combination thereof The achievable precision (sensitivity, resolution) of the sensing process depends critically on the proper evaluation (e.g. determination of the positions of the dips in the arrangements according to FIG. 11, or of corresponding intensity peaks which will typically be observed in the arrangements of FIGS. 7, 8, 9 working in the domain of reflection).

Two preferred embodiments giving a high precision of the results derived in the sensing process are as follows:

Method 1: Recording the intensity dips or peaks in time or space directly, and using a procedure for fitting model curves to the data for determining the dip/peak position also in the presence of disturbances (noise). In the case of FIG. 11, the wavelength could be varied exactly as shown in FIG. 11(b).

Method 2: Modulating the parameter (the wavelength in the example of FIG. 11) in a more complicated (nonlinear) way, e.g. by adding a periodic modulation at a frequency f to the signal shown in FIG. 11(b). Then, lock-in techniques can be used instead of recording the dips, and in many cases, more accuracy can be achieved than with other methods. The phase-locked demodulation of the detector output signal is preferentially performed at the same frequency for at a higher frequency (e.g. 2f) of the modulating signal.

Figure 12:
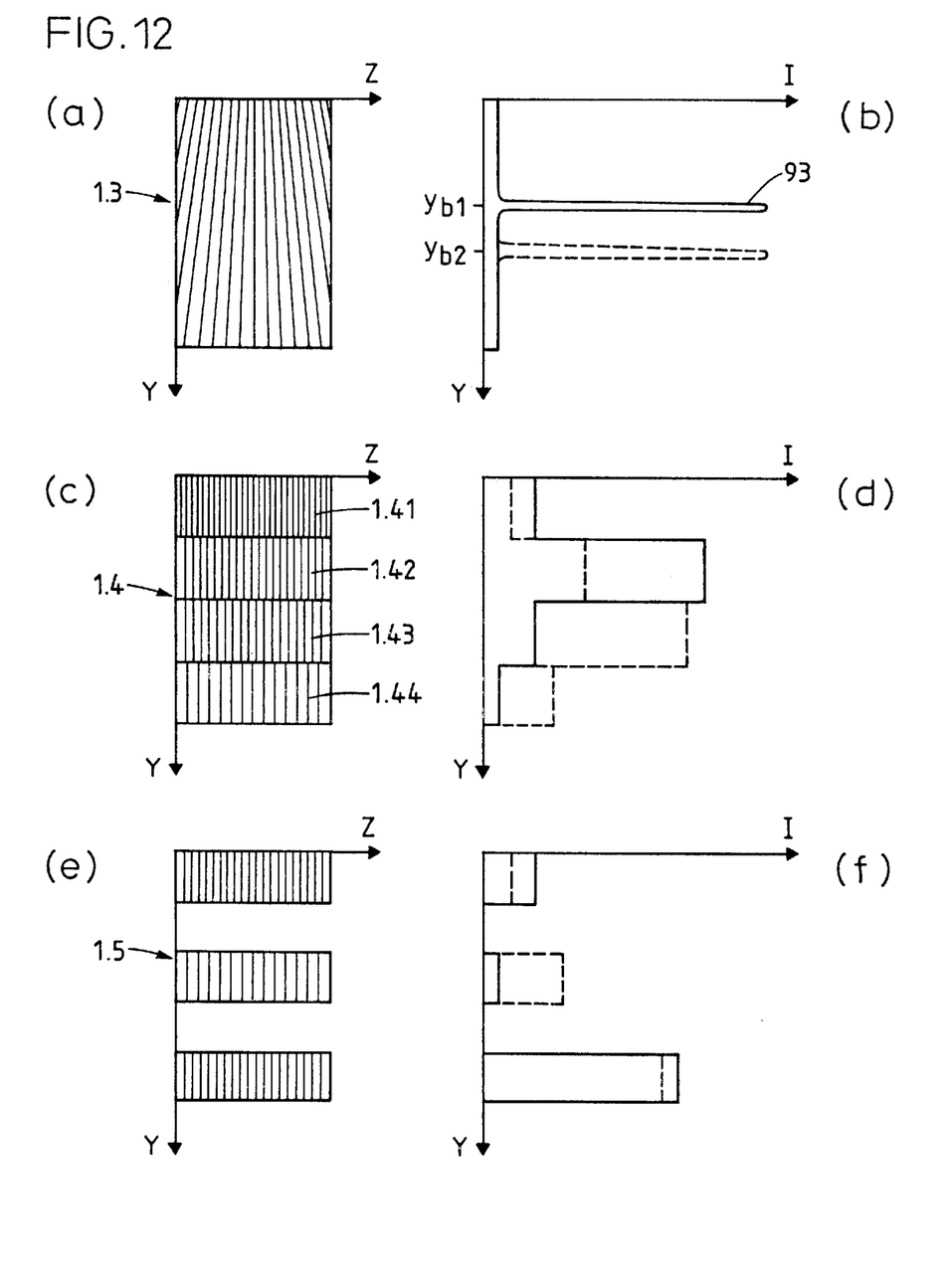
FIG. 12 shows various embodiments of resonant waveguide grating structures for an IO sensor according to the invention, and their spatial output signals.

In the embodiments of FIGS. 5 and 6, chirped gratings were used as resonant waveguide grating structures. Other resonant waveguide grating structures are possible for use in the invention, the most simple of them being a homogeneous grating. As a further development of the idea of the chirped grating, FIG. 12 shows various embodiments of resonant waveguide grating structures 1.3–1.6 for an IO sensor according to the invention (FIGS. 12(a), (c), (e) and (g)), and their electromagnetic field intensities I versus the y coordinate (FIGS. 12(b), (d), (f) and (h)). The intensity I(y) of an electromagnetic field resonantly excited via a chirped grating 1.3 (FIG. 12(a)) exhibits a sharp peak 93 at a certain position $y_{b1}$ (FIG. 12(b); cf. FIG. 5(a)). In order to determine the exact position of the peak, the intensity signal of FIG. 12(b) can be fitted (using, e.g., a Gaussian intensity distribution model). The peak 93 moves from its original position $y_{b1}$ (full line) towards a different position $y_{b2}$ (dashed line) if a parameter of the waveguide or of the incident light such as the wavelength is changed. As explained with reference to FIGS. 5 and 6, the peak 93 can be clamped or stabilized at a certain y position by providing a controlled closed-loop system. The discrete grating 1.4 of FIG. 12(c) is obtained by dividing the chirped grating 1.3 of FIG. 12(a) into a plurality of regions 1.41–1.44, i.e., stripes in y direction, and providing in each region 1.41–1.44 a homogeneous grating with a grating period which is equal to an average grating period of the corresponding region in the chirped grating 1.3. For this discrete grating structure 1.4, the intensity distribution I(y) generally exhibits different levels for the different regions 1.41–1.44; the levels change with varying light parameters or waveguide parameters (FIG. 12(d)). The value of a measurand M can be evaluated by interpolating between two intensity distributions for known measurands $M_1$, $M_2$. Alternatively, the intensity levels can also be clamped or stabilized to be constant by providing a controlled closed-loop system 5. For applying this principle according to the invention, the discrete gratings need not be adjacent to each other, and their grating periods need not increase monotonously with the y coordinate, as is the case for the resonant waveguide grating structure 1.5 of FIG. 12(e); a possible corresponding intensity distribution I(y) is shown in FIG. 12(f). The embodiment of FIG. 12(g) has a non-periodic resonant waveguide grating structure 1.6. It exhibits a generally irregular intensity distribution I(y) such as sketched in FIG. 12(h). It might seem unpractical to deal with such irregular intensity distributions I(y); however, it is quite simple to clamp or stabilize the distribution I(y) by providing a controlled closed-loop system 5 according to the invention, as in the previous embodiments. The embodiment of FIG. 12(g) has the advantages that imperfections of the resonant waveguide grating structure 1.6 do not disturb the measurements, and that a mathematical fit of a measured intensity distribution I(y) need not be performed.

Referring again to FIGS. 12(c)–(h), a method for the signal evaluation shall be presented. Supposed that the output signals $S_1$ and $S_2$ are known for known measurand values $M_1$ and $M_2$, respectively. Then a measurand value M can be straightforward evaluated from a detected output signal s using the formula $$M = s \otimes (M_1 \cdot s_1 + M_2 \cdot s_2)/s \otimes (S_1+S_2), \quad (2)$$

where $$(s \otimes s_1)(y) \equiv s(y) \otimes s_1(y) = \int_{-\infty}^{+\infty} s(\alpha) \cdot s_1(\alpha + y) d\alpha \quad (3)$$

denotes the correlation operation. Alternatively, for clamping or stabilizing the signal s(y, t) using, e.g., a wavelength-controlled feedback loop 5, the wavelength must at all times be chosen such that the equation $$s(y,t) \otimes (S_2 - s_1)(y) = 0 \quad (4)$$

holds for all positions y and all times t.

Figure 13:
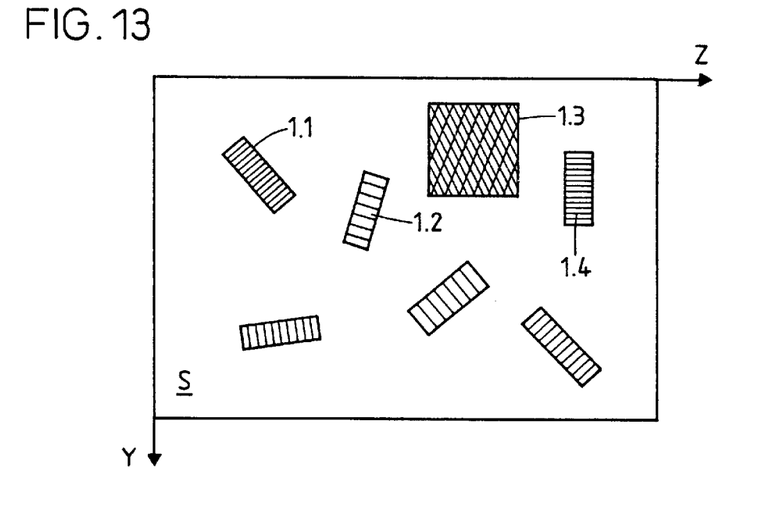
FIG. 13 shows a further embodiment of a multiple arrangement of IO sensors according to the invention.

The embodiment of FIG. 13 shown in a top view (in analogy to FIG. 9(a)) applies the principle of FIGS. 12(g) and (h) to a multiple arrangement of IO sensors. The resonant waveguide grating structures 1.1, 1.2, ... need not be in rows or columns. The grating structures 1.1, 1.2, ... themselves need not be periodic. The resonant waveguide grating structure 1.3 is an example of two superposed gratings.

In summary, the advantages of the invention result from the possibility of independent simultaneous ("parallel") measurements with the sensors. In addition, there are also the following advantages, whose importance can depend on the actual application:

The size needed per measuring unit is reduced.

The chips incorporate a high-density array of individual measuring pads which can be read out in parallel (or sequentially by scanning). This is important for multi-channel parallel detection, for example in biosensing applications.

Not only the pads themselves, but also the whole chip has a high functionality.

Works for different IO sensing principles (e.g. refractometry, absorption, scattering, geometrical sensors [layer thickness changes]).

Easy, low-cost fabrication of sensor chips is possible—same technology for a great variety of applications.

Often, the detector requirements (area) are also relaxed.

Often, the illumination is eased (less area to be illuminated).

What is claimed is:

1. An integrated-optical chemical and/or biochemical sensor comprising:

a resonant waveguide grating structure defining a surface plane;

a sensing area arranged in the immediate vicinity of the resonant waveguide grating structure and adapted for being contacted by a liquid substance;

means for emitting electromagnetic radiation towards the resonant waveguide grating structure;

the means for emitting electromagnetic radiation comprising means for varying at least one parameter of the emitted electromagnetic radiation;

the mutual arrangement of the resonant waveguide grating structure and the means for emitting electromagnetic radiation being such that the angles of incidence with respect to a normal line on said surface plane are greater than −90° and smaller than +90°, and detector means for detecting electromagnetic radiation excident from the resonant waveguide grating structure;

the mutual arrangement of the resonant waveguide grating structure and the detector means being such that the angles of excidence with respect to a normal line on said surface plane are greater than −90° and smaller than +90°, and differ from the angles of incidence.

2. A sensor according to claim 1, wherein the parameter varied by said means (3, 31, 32) for varying is an angle of incidence ($\theta_i$), the wavelength ($\lambda$), the polarization, the spectral distribution and/or the wavefront.

3. A sensor according to claim 2, wherein said means (3, 31, 32) for varying comprise a rotatable mirror (32), a movable light source (3), a movable lens (31) and/or an array of light sources (3.1–3.5).

4. A sensor according to claim 1, wherein said means (3) for emitting electromagnetic radiation (21) comprise a tunable narrow-band light source such as a vertical cavity surface emitting laser (VCSEL), a distributed feedback (DFB) laser and/or a distributed Bragg reflector (DBR) laser.

5. A sensor according to claim 1, wherein said means (3) for emitting electromagnetic radiation (21) comprise means for emitting a plurality of, preferably discrete, wavelengths, angles of incidence and/or polarizations.

6. A sensor according to claim 1, wherein said resonant waveguide grating structure (1, 1.1, 1.2, . . . ) comprises at least one singly periodic, multiply periodic and/or chirped grating, and/or several superposed gratings.

7. A sensor according to claim 1, wherein said detector means (4, 4.1, 4.2, . . . ) comprise a single detector or a one- or two-dimensional array of detectors, preferably charge-coupled device (CCD) detectors.

8. A sensor according to claim 1, comprising means (6) for imaging said resonant waveguide grating structure (1, 1.1, 1.2, . . . ) onto said detector means (4, 4.1, . . . ), or means for transforming a variation of the angle of excidence ($\theta_o$), into a variation of the light position on said detector means (4, 4.1, 4.2, . . . ).

9. A sensor according to claim 1, comprising means (5) for providing a feedback from said detector means (4) to said means (3) for emitting electromagnetic radiation (21), thus establishing a controlled closed-loop system.

10. A sensor according to claim 1, wherein said resonant waveguide grating structure (1, 1.1, 1.2, . . . ) is coated with a sensing layer (SL) suitable for a chemical reaction with a substance to be sensed.

11. A multiple one-, two- or three-dimensional arrangement of a plurality of sensors (S1, S2, . . . ) such as defined in claim 1.

12. A multiple one- or two-dimensional arrangement of sensors (S1, S2, . . . ) according to claim 11, wherein the resonant waveguide grating structures (1, 1.1, 1.2, . . . ) are arranged in a single surface plane (10).

13. A multiple arrangement of sensors (S1, S2, . . . ) according to claim 11, wherein at least one measurement sensor (S) is provided for sensing a chemical and/or biochemical substance, and at least one reference sensor (R) is provided for deriving a reference signal.

14. A multiple arrangement of sensors (S1, S2, . . . ) according to claim 13, wherein each measurement sensor (S) is adjacent to at least two, and preferably to four, reference sensors (R).

15. A method for integrated-optically sensing a chemical and/or biochemical liquid substance, comprising the steps of:

providing a resonant waveguide grating structure defining a surface plane, and a sensing area arranged in the immediate vicinity of the resonant waveguide grating structure and adapted for being contacted by the liquid substance;

bringing the liquid substance into contact with the sensing area;

emitting electromagnetic radiation towards the resonant waveguide grating structure, the angles of incidence with respect to a normal line on said surface plane being greater than −90° and smaller than +90°;

exciting a resonant electromagnetic field in the resonant waveguide grating structure by means of the emitted electromagnetic radiation;

causing an interaction of the liquid substance with the resonant electromagnetic field;

varying at least one parameter of the emitted electromagnetic radiation; and detecting electromagnetic radiation excident from the resonant waveguide grating structure, the angles of excidence with respect to a normal line on said surface plane being greater than −90° and smaller than +90°, and differ from the angles of incidence.

16. A method according to claim 15, wherein the parameter varied is an angle of incidence ($\theta_i$), the wavelength ($\lambda$), the polarization, the spectral distribution and/or the wavefront.

17. A method according to claim 15, wherein the emitted electromagnetic radiation (21) is within one or more narrow spectral bands, or features a plurality of, preferably discrete, wavelengths, angles of incidence and/or polarizations.

18. A method according to claim 15, wherein the resonant electromagnetic field (22) is excited using a first diffraction order and the excident electromagnetic radiation (23) is outcoupled via a second, different diffraction order.

19. A method according to claim 15, wherein the position of at least a part of the emerging electromagnetic radiation (23) is detected, or the intensity of at least a part of the emerging electromagnetic radiation (25) is detected.

20. A method according to claim 15, wherein a variation of the angle of excidence ($\theta_o$) is transformed into a variation of a light position, or said resonant waveguide grating structure (1, 1.1, 1.2, . . . )is imaged onto an image plane (40).

21. A method according to claim 15, wherein at least one parameter of the emitted electromagnetic radiation (21) is controlled by at least one parameter of the detected electromagnetic radiation (23, 25).

22. A method according to claim 21, wherein the radiation excident (23, 25) from the resonant waveguide grating structure is stabilized to be constant by controlling at least one parameter of the emitted electromagnetic radiation (21).

23. A method according to claim 15, wherein the mathematical correlation of at least two signals (s, $s_1$), detected at different times (t) and/or at different locations (y), is used to derive an output signal.

* * * * *